July 14, 1964 G. MERRILL Plant Pat. 2,425
PEACH TREE
Filed Feb. 14, 1963
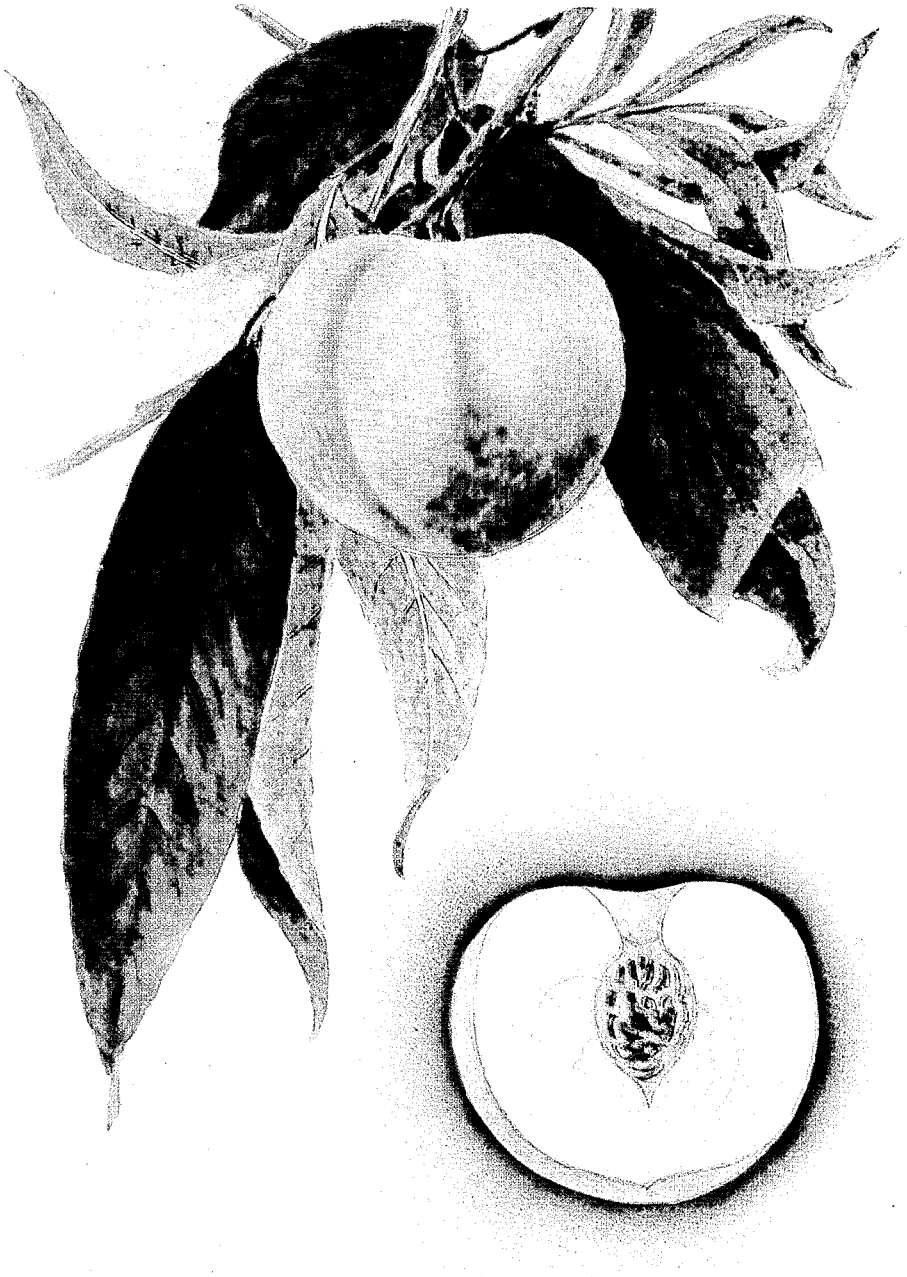
WITNESS
Addison E. Avery
GRANT MERRILL
INVENTOR
HUEBNER & WORREL
ATTORNEYS
BY Richard M. Worrel United States Patent Office Plant Pat. 2,425
Patented July 14, 1964

2,425
PEACH TREE

Grant Merrill, P.O. Box 392, Red Bluff, Calif.

Filed Feb. 14, 1963, Ser. No. 258,658
1 Claim. (Cl. Plt.—43)

The present invention relates to a peach tree and more particularly to a new and distinct variety thereof broadly characterized by vigorous and regular bearing; moderately early bloom; and large, firm, fine-textured, yellow-fleshed freestone peaches having a minimum of split pits.

The instant variety blooms about the same time as the Elberta (unpatented) peach tree. Its fruit ripens at about the same time as the Rio Oso Gem peach tree of U.S. Plant Patent No. 84 and the Merricle L–14 of U.S. Plant Patent No. 1,954, the latter of which the instant variety most closely resembles. In further comparison, its fruit retains the high color, good firmness and fine flesh texture of the Merricle L–14 peach but is distinctive therefrom by being larger in size and having fewer split pits.

The splitting of the pits in peaches has presented a serious problem to growers. When such splitting occurs, the stem end of the peach frequently opens, exposing the flesh to the atmosphere, causing fermentation and other spoilage and admitting insects, dirt and other contaminants. Also, peaches having split pits cannot readily be handled by mechanical pit-removing machines which are designed to remove whole pits. When portions of a pit are allowed to remain after mechanical pitting, they frequently damage subsequent mechanical processing equipment such as is employed in slicing and canning operations and the like or if the pit is processed therewith an inferior product results. Fresh fruit packers must cull out any peaches having split pits no matter how attractive they may appear. Therefore, a primary object of the plant breeding procedures which resulted in the development of this new peach variety was to achieve a larger peach having fewer split pits.

Further objects and advantages will become more fully apparent in the subsequent description in the specification.

I originated the present variety of peach tree on my farm near Red Bluff, Tehama County, California, in the following manner: A July Elberta peach tree of U.S. Plant Patent No. 15 was crossed with a Maxine (unpatented) peach tree. The resulting tree was crossed with a J. H. Hale (unpatented) peach tree. Such crossing is expressed in the formula (J. H. Hale × (July Elberta × Maxine)). Buds from the new tree were placed in a seedling peach tree in an isolation plot on my farm at Corning, Tehama County, California. The tree fruited in August 1962 and the fruit and tree characteristics resulting from such budding proved identical to those of the original tree.

The accompanying drawing is a water color painting of a characteristic twig of the subject peach tree bearing foliage and a mature fruit and additionally, showing a fruit of the subject variety divided on its suture plane to reveal flash coloration and pit characteristics.

Referring more specifically to the pomological details of this new and distinct variety of peach tree, the following has been observed under the ecological conditions prevailing at my farm near Red Bluff, Tehama County, California, and is an outline description thereof All major color plate identifications are by reference to Maerz and Paul Dictionary of Color.

*Tree*

Size: Large, vigorous, vase formed and moderately open by pruning, and regular bearer.
Trunk: Medium slender, medium shaggy.
Branches: Lenticels, medium in quantity, medium sized.
Leaves (selected from midportion of vigorous unbranched terminal shoot):
*Size.*—Large.
*Length.*—7″ to 8½″, average 7¾″.
*Width.*—1⅜″ to 1¾″, average 1⅝″.
*Form.*—Lanceolate, tip acuminate, medium thick.
*Color.*—Upper surface, Medium Green (21–J–7); underside, Light Green (20–E–4); midrib, Light Yellowish Green (18–K–2).
*Class.*—(Meader and Blade: Proceedings of Am. Soc. Hor. Sc., vol. 37, page 206).—2 and 3.
*Margin.*—Glandular, Crenate.
*Petiole.*—Medium long, medium slender.
*Stipules.*—At base of leaf, falling off early.
Flower buds: Medium size, truncate to obtuse, plump, free, pubescent.
Flowers: Medium early, medium size, pink. Pollen—abundant.

*Fruit*

Maturity when described, firm to soft ripe.

Size: Large, variable.
*Axial diameter.*—2½″ to 3¾″, average 3″.
*Transverse in suture plane.*—2½″ to 3¾″, average 3″.
*At right angle to suture plane.*—2¾″ to 3¼″, average 2⅞″.
Form: Variable, globose to some slightly flattened in suture plane.
*Suture.*—Distinct, shallow line which extends from base to apex, has slight depression beyond pistil point.
*Cavity.*—Abrupt, elongated in suture plane, suture showing on both sides.
*Depth.*—⅜″ to ⅝″, average ½″.
*Breadth.*—⅝″ to 1⅜″, average ⅞″.
*Base.*—Retuse to obcordate.
*Apex.*—Retuse to mucronate, some cuspidate, some depressed.
*Stem.*—Short, length ⅜″, diameter ⅛″ to 5/32″.
Skin: Medium thick, medium tough, tenacious to flesh.
*Color.*—50% to 90% Bright Red (3–L–10).
*Under color.*—Yellowish Orange (10–L–11).
*Down.*—Scant, short, does not roll up when rubbed.
Flesh:
*Color.*—Deep Yellow (9–L–4), streaked and mottled throughout, particularly near the base with red next to the pit cavity (1–K–10).
*Surface of pit cavity.*—Dark Red (4–K–7).
*Amygdalin.*—Moderate.
*Texture.*—Fine, meaty, melting.
*Fibers.*—Fine and tender.
*Ripens.*—Evenly.
*Flavor.*—Delicate, subacid.
*Aroma.*—Distinct.
*Eating quality.*—Good.
Stone: Free, adheres to flesh somewhat at stem end on ventral and dorsal edges.
*Fibers.*—Fleshy and moderately short.
*Size.*—Medium.

*Length.*—1½" to 1¾", average 1⅝".
*Breadth.*—⅞" to 1½", average 1⅛".
*Thickness.*—⅝" to 1", average 13/16".
*Form.*—Ovate with pronounced tip.
*Base.*—Usually oblique.
*Sides.*—Usually equal.
*Apex.*—Cuspidate.
*Surface.*—Usually flattened toward base on both sides or either side, usually pitted toward base, furrowed toward base and on ventral and dorsal edges.
*Pits.*—Circular and elongated.
*Ventral edge.*—Thick, without wing.
*Dorsal edge.*—Narrow, irregular grooves throughout.
*Color.*—Light Brown (6–I–7).

Use: Fresh market, local and distant.
*Keeping quality.*—Good.
*Shipping quality.*—Good.

Although the new variety of peach tree possesses the described characteristics under the growing conditions in Tehama County, California, having been first observed near Red Bluff, Tehama County, California, at the northern end of the Sacramento Valley, and later confirmed at Corning in Tehama County, California, it is to be understood that variation of the usual magnitude in characteristics incident to the growing conditions, fertilization, pruning and pest control are to be expected.

Having thus described and illustrated my new variety of peach tree, what is claimed as new and described to be secured by Letters Patent is:

A new and distinct variety of peach tree substantially as illustrated and described and which is characterized by its vigorous growth; its moderately early blooming at about the same time as the Elberta (unpatented) peach tree; and its regular and heavy bearing of large, freestone, yellow-fleshed fruit of firm, fine texture which ripens approximately at the same time as fruit of the Rio Oso Gem peach tree of U.S. Plant Patent No. 84 and the Merricle L–14 peach tree of U.S. Plant Patent No. 1,954, which it most nearly resembles but from which it is distinguished in its greater vigor and productivity and in its bearing of larger, finer fruit having pits with a greater resistance to splitting.

No references cited.